US00PP12438P2

(12) United States Plant Patent
Zaiger et al.

(10) Patent No.: US PP12,438 P2
(45) Date of Patent: Mar. 5, 2002

(54) NECTARINE TREE NAMED 'EARLIHONEY'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 15 days.

(21) Appl. No.: 09/835,764

(22) Filed: Apr. 16, 2001

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Anne Marie Grünberg

(57) ABSTRACT

A new and unique variety of nectarine tree (*Prunus persica* var. *nucipersica*) that has the following distinct characteristics, which are desirable in a new variety. The tree and its fruit are characterized with the tree budded on 'Nemaguard' Rootstock (non-patented), grown on Hanford sandy loam soil with Storie Index rating 95, in USDA Hardiness Zone 9, near Modesto, Calif., with standard commercial fruit growing practices, such as pruning, thinning, spraying, irrigation and fertilization.

1. Heavy and regular production of fruit.
2. Fruit with firm, yellow flesh, good storage and shipping quality.
3. Fruit with an attractive red skin color.
4. Fruit with very good flavor and eating quality.
5. Fruit with the ability to remain firm on the tree approximately 8 days after maturity (shipping ripe).
6. Vigorous, upright growth.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine and peach trees, which are known to use and mentioned herein, are 'Tasty Gold' Nectarine (U.S. Plant Pat. No. 5,623), 'May Grand' Nectarine (U.S. Plant Pat. No. 2,794). 'Early Sun Grand' Nectarine (U.S. Plant Pat. No. 1,420), 'Honey Kist' Nectarine (U.S. Plant Pat. No. 9,333) and 'Royal Gold' Peach (U.S. Plant Pat. No. 2,663).

ORIGIN OF VARIETY

The present variety of nectarine tree, (*Prunus persica* var. *nucipersica*), was originated by us in our experimental orchard located near Modesto, Calif., as a first generation cross between two selected seedlings with the field identification numbers 38EB16 and 10LA512. The maternal parent (38EB16) originated as a first generation cross between a high-colored nectarine of unknown parentage and 'Tasty Gold' Nectarine (U.S. Plant Pat. No. 5,623). The paternal parent (10LA512) originated as a first generation cross between two selected seedlings with field identification numbers 36EB86 and 9GC175. The maternal parent (36EB86) originated as a second-generation seedling that was selected from a cross between 'May Grand' Nectarine (U.S. Plant Pat. No. 2,794) and a peach of unknown parentage. The pollen parent (9GC175) originated as a second-generation seedling of a cross between an open pollinated seedling of 'Early Sun Grand' Nectarine (U.S. Plant Pat. No. 1,420) and 'Royal Gold' Peach (U.S. Plant Pat. No. 2,663). A large group of these first generation seedlings growing on their own root were planted and maintained under careful observation by us. One such seedling, which is of the present variety, having especially desirable fruit characteristics was selected in 1993 for asexual reproduction and commercialization.

ASEXUAL REPRODUCTION OF THE VARIETY

Asexual reproduction of the new and distinct variety of nectarine tree was by budding on 'Nemaguard' Rootstock (non-patented), as performed by us in our experimental orchard located near Modesto, Calif., and shows that reproductions run true to the original tree and all characteristics of the tree and the fruit are established and transmitted through succeeding asexual propagations.

SUMMARY OF THE VARIETY

The new and distinct variety of nectarine tree is of large size, vigorous, upright growth, a regular and productive bearer of medium to large size, firm, yellow flesh, clingstone fruit that is mild, sweet and sub-acid with very good flavor and eating quality. The fruit is further characterized by its attractive red skin color, its ability to remain firm on the tree approximately 8 days after maturity (shipping ripe) and, in comparison to the sub-acid 'Honey Kist' Nectarine, the new variety is similar in flavor and eating quality, but is approximately 12 days earlier in maturity. In comparison to the nectarines 'May Grand', 'Tasty Gold' and 'Early Sun Grand', which have the normal acidic flavor, the present variety has a sub-acidic, sweet flavor with a very desirable eating quality, all varieties ripening in the early maturing season.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe), and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 7 year old specimens budded to 'Nemaguard' Rootstock (non-patented) and grown near Modesto, Calif., with color terminology (except those in common terms) in accordance with Reinhold Color Atlas by A. Kornerup and J. H. Wanscher.

Tree:

*Size.*—Large. Pruned 10 to 12 feet in height and width, primarily for economic harvesting of fruit.

*Vigor.*—Vigorous. Grows to a height of 5 to 6 feet the first growing season. Pruned to 3 to 5 feet in height the first dormant season when selecting primary scaffolds.

*Form.*—Upright, usually pruned to vase shape. Heavy fruit set increases width of tree.

*Fertility.*—Self-fertile.

*Productivity.*—Productive. Amount of fruit set is 1½ to several times more than desired for normal crop load. Fruit is thinned and spaced to the desired number to develop marketable fruit size.

*Bearer.*—Regular. Produced adequate fruit set for 6 consecutive years. No alternate bearing observed.

*Density.*—Medium dense. Pruned to a vase shape to allow more sunlight to the center of the tree to enhance fruit color and Brix.

*Growth.*—Normal upright growth with a tendency to spread with heavy crop load.

*Hardiness.*—Hardiness tested in USDA Zone 9. Winter chilling requirement estimated to be 600 hours below 45° F. Hardy in all stone fruit growing areas of California.

Trunk:

*Size.*—Medium stocky. Circumference of 21 inches at 12 inches above the ground on a 7 year old tree.

*Texture.*—Medium shaggy. Roughness increases with age.

*Color.*—Grayish brown to leather brown (6-E-3) to (6-E-6).

Branches:

*Size.*—Medium. Circumference averages 9 inches at 36 inches above the ground.

*Surface texture.*—Smooth to medium rough. Roughness increases with age of branch.

*Lenticels.*—Size — medium. Average number of 11 per four square inch surface. Average length ⅛ inch. Average width 3/64 inch. Color — golden brown to light brown (5-D-4) to (5-D-7).

*Color.*—New growth varies from olive green to moss green (1-E-4) to (1-E-7). Mature growth varies from brown to beaver brown (5-E-4) to (5-E-6). Color becomes darker with age of branch.

Leaves:

*Size.*—Large. Average length 6 inches. Average width 1½ inches.

*Form.*—Lanceolate.

*Apex.*—Acuminate.

*Base.*—Cuneate.

*Margin.*—Serrate.

*Thickness.*—Medium, normal for nectarines.

*Surface.*—Upper surface relatively smooth except for small indented areas over leaf veins, glabrous. Lower surface relatively smooth except for small ridges created by midrib and pinnate venation, glabrous.

*Petiole.*—Size — medium. Average length 25/64 inch. Average thickness 1/16 inch. Color varies from yellowish green to grayish green (30-C-8) to (30-D-8).

*Glands.*—Type — reniform. Number varies from 1 to 4. Average number 2. Average diameter 1/16 inch. Color varies with age of leaf from maize yellow to Cardinal red (4-B-5) to (10-D-7). Becomes darker on older leaves. Located on the upper portion of petiole and the lower portion of the leaf blade.

*Color.*—Upper surface — green to parsley green (30-F-5) to (30-F-8). Lower surface — grayish green to dull green (30-E-6) to (30-E-8).

Flower buds:

*Size.*—Medium to large. Average length 39/64 inch. Average diameter 25/64 inch. 3 days before bloom.

*Form.*—Plump, conical, becomes elongated as bud matures.

*Pubescence.*—Pubescent only on outer surface of sepals.

*Shape.*—Elongated at maturity.

*Color.*—Pink to pastel pink (11-A-3) to (11-A-5).

*Hardiness.*—Hardy in all stone fruit growing areas of California.

*Pedicel.*—Average length 9/64 inch. Average width 5/64 inch. Color — light green to grayish green (29-A-5) to (29-B-5).

Flowers:

*Size.*—Large, showy. Average height ¾ inch. Average diameter 1⅜ inch.

*Petals.*—Number — 5, alternately arranged to sepals. Shape — elliptical, smooth to slightly scalloped edges. Average length ¾ inch. Average width 37/64 inch. Color — pink (11-A-4).

*Sepals.*—Number — 5. Alternately arranged with petals. Shape — elongated. Upper surface color — butter yellow (4-A-5) changing to fox red (8-D-7) near outer edges, glabrous. Lower surface color — Venetian red (8-D-8), pubescent. Average length 7/32 inch. Average width 9/64 inch.

*Pollen.*—Present, self-fertile. Color — light yellow to yellow (3-A-3) to (3-A-5).

*Stamens.*—Number varies from 35–43 per flower. Average number 39. Average length 27/64 inch. Filament color white to whitish yellow (1-A-1) to (1-A-2), turning light pink with age of bloom. Anther color — cardinal red (10-D-8).

*Pistil.*—Normally one, varies from 1 to 2. Not pubescent. Average length 41/64 inch. Color — milk white to pale yellow (1-A-2) to (1-A-3). Stigma positioned 5/64 inch above anthers.

*Aroma.*—None.

*Pedicel.*—Average length 9/64 inch. Average width 5/64 inch. Color — grayish green (30-C-6).

*Color.*—Pink to pastel pink (11-A-3) to (11-A-5). Color fades with age of bloom.

*Blooming period.*—Date of first bloom Feb. 27, 2000. Date of petal fall Mar. 8, 2000. Varies slightly with climatic conditions.

Fruit:

*Maturity when described.*—Firm ripe.

*Date of first picking.*—Jun. 1, 2000.

*Date of last picking.*—Jun. 8, 2000. Varies slightly with climatic conditions.

*Size.*—Medium to large. Average diameter axially 2½ inches to 2⅞ inches. Average transversely in suture plane 2⅜ to 2¾ inches. Avearge weight 182 grams.

*Form.*—Globose.

*Suture.*—Nearly smooth, extends from base to apex.

*Ventral surface.*—Nearly round, very slightly lipped.

*Apex.*—Nearly rounded, varies from round to very slight point.

*Base.*—Retuse.

*Cavity.*—Rounded to slightly elongated in the suture plane. Average depth 7/16 inch. Average breadth ¾ inch.

Stem:

*Size.*—Average length 7/16 inch. Average width ⅛ inch. Enlarged at point of attachment.

*Color.*—Yellowish green to olive green (1-B-5) to (1-C-4).

Flesh:

*Ripens.*—Relatively even, only slightly earlier near apex.

*Texture.*—Firm, meaty.

*Fibers.*—Few, small, tender.

*Aroma.*—Moderate.

*Amygdalin.*—Undetected.

*Juice.*—Moderate amount, enhances flavor, soluble solids of 9.3° Brix.

*Eating quality.*—Very good.

*Flavor.*—Very good, mild, sweet, sub-acid.

*Color.*—Varies from butter yellow to maize yellow (4-A-5) to (4-A-6). Pit cavity varies from grayish yellow to olive yellow (4-B-5) to (4-C-6). Very slight bleeding of light red (10-A-6) into flesh near apex.

Skin:

*Thickness.*—Medium, normal for nectarines. Shows minimal scarring in picking and packing trials.

*Texture.*—Medium, tenacious to flesh.

*Down.*—Wanting.

*Tendency to crack.*—None.

*Astringency.*—None.

*Color.*—Pale yellow to light yellow (4-A-4) to (4-A-6) ground color. Overspread with Turkish red to Cardinal red (10-C-8) to (10-D-8). Very small, randomly spaced areas of ground color showing, leaving a speckling pattern to some areas of skin.

Stone:

*Type.*—Clingstone.

*Size.*—Large. Average length 1½ inches. Average width 1⅛ inches. Average thickness ¾ inch.

*Form.*—Ovoid.

*Base.*—Rounded.

*Apex.*—Cuspidate, very short.

*Surface.*—Irregularly furrowed toward apex, pitted toward base. Pits vary from round to elongated. Ridges relatively wide and rounded. One long groove one each side of suture extending from base to apex.

*Sides.*—Mostly unequal, varies from unequal to equal. Most stones having one side extending further from suture plane.

*Tendency to split.*—Very slight.

*Color.*—Light tan to light brown, when dry (5-B-4) to (5-C-7).

Kernel: Average length 49/64 inch. Average width 31/64 inch. Skin color varies from tan to golden orange (4-B-5) to (5-B-5), when dry.

*Taste.*—Bitter.

*Amygdalin.*—Abundant.

Use: Dessert. Market, local and long distance.

Storage quality: Good, fruit holds firm for 2 weeks in cold storage with no internal breakdown of flesh or appreciable loss of eating quality.

Shipping quality: Minimal flesh bruising and skin scarring in packing and shipping trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety of selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of necatrine tree, substantially as illustrated and described, characterized by its large size, vigorous, upright growth, and being a productive and regular bearer of yellow flesh, clingstone fruit with good storage and shipping ability; the fruit is further characterized by having a mild, sweet, sub-acidic flavor and good eating quality, holding firm on the tree approximately 8 days after maturity (shipping ripe) and, in comparison to the sub-acid nectarine 'Honey Kist' (U.S. Plant Pat. No. 9,333), the new variety is approximately 12 days earlier in maturity.

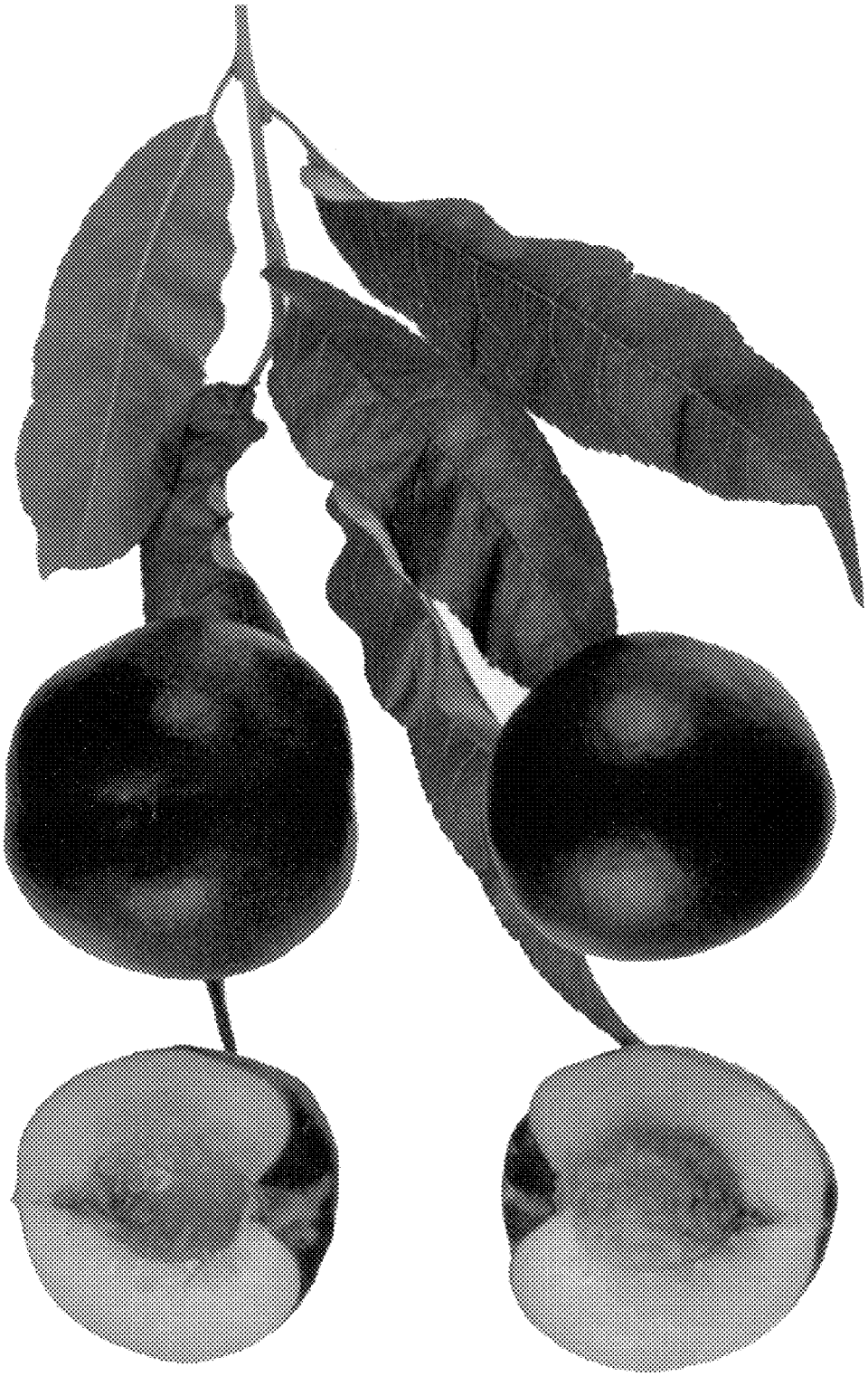

* * * * *